United States Patent [19]

Nishina et al.

[11] Patent Number: 4,936,298
[45] Date of Patent: Jun. 26, 1990

[54] OXYGEN PRODUCER ARTIFICIAL RESPIRATOR

[76] Inventors: Edward T. Nishina, 78 6401 Mamalahoa HY, Holualoa, Hi. 96725; George Spector, 233 Broadway RM 3815, New York, N.Y. 10007

[21] Appl. No.: 291,580
[22] Filed: Dec. 29, 1988
[51] Int. Cl.⁵ .................. A62B 7/00; A62B 9/06
[52] U.S. Cl. .................. 128/205.13; 128/205.25; 128/206.26; 128/206.29
[58] Field of Search ............ 128/204.18, 205.13, 128/205.25, 206.26, 206.29, 200.24, 200.26, 201.26, 206.21, 206.24, 206.27, 207.12, 207.14, 207.16, 207.17

[56] References Cited

U.S. PATENT DOCUMENTS

| | | | |
|---|---|---|---|
| 1,197,232 | 9/1916 | Pierpont | 128/205.13 |
| 1,337,225 | 4/1920 | Heald | 128/205.13 |
| 2,857,911 | 10/1958 | Bennett | 128/206.24 |
| 3,009,459 | 11/1961 | Ruben | 128/205.13 |
| 3,043,302 | 7/1962 | Spears et al. | 128/205.25 |
| 3,090,380 | 5/1963 | Dold | 128/205.13 |
| 3,091,236 | 5/1963 | Delbert | 128/205.13 |
| 4,226,233 | 10/1980 | Kritzer | 128/204.18 |
| 4,513,741 | 4/1985 | Demi | 128/205.25 |

FOREIGN PATENT DOCUMENTS

| | | | |
|---|---|---|---|
| 643948 | 4/1937 | Fed. Rep. of Germany | 128/206.26 |
| 2446115 | 9/1980 | France | 128/205.13 |
| 775911 | 5/1957 | United Kingdom | 128/206.26 |
| 1238649 | 7/1971 | United Kingdom | 128/205.13 |

*Primary Examiner*—Edgar S. Burr
*Assistant Examiner*—Kimberly L. Asher

[57] ABSTRACT

An artificial respiration device is provided and consists of an elastic head band affixed to a mask for securing the mask over mouth of a person with a removable hollow nipple threaded within the mask extending into the mouth. A manually operated mechanism is connected to the mask for supplying fresh air one-way through the nipple and into lungs of the person so that expired air can exit out through the person's nose into the ambient atmosphere.

1 Claim, 1 Drawing Sheet

OXYGEN PRODUCER ARTIFICIAL RESPIRATOR

BACKGROUND OF THE INVENTION

The instant invention relates generally to manually operated resuscitators and more specifically it relates to an artificial respiration device.

Numerous manually operated resuscitators have been provided in prior art that are adapted to introduce air into the lungs of people who are in need of breathing. For example, U.S. Pat. Nos. 3,009,459; 3,046,978 and 3,216,413 all are illustrative of such prior art. While these units may be suitable for the particular purpose to which they address, they would not be as suitable for the purposes of the present invention as heretofore described.

SUMMARY OF THE INVENTION

A primary object of the present invention is to provide an artificial respiration device that will overcome the shortcomings of the prior art devices.

Another object is to provide an artificial respiration device that will supply air into a person's mouth and lungs so as to eliminate the need for mouth-to-mouth resuscitation.

An additional object is to provide an artificial respiration device in which during operation of the device a portion of the air therefrom will cause the contacting flange of the mask to expand to form a tight seal about the mouth.

A further object is to provide an artificial respiration device that is simple and easy to use.

A still further object is to provide an artificial respiration device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
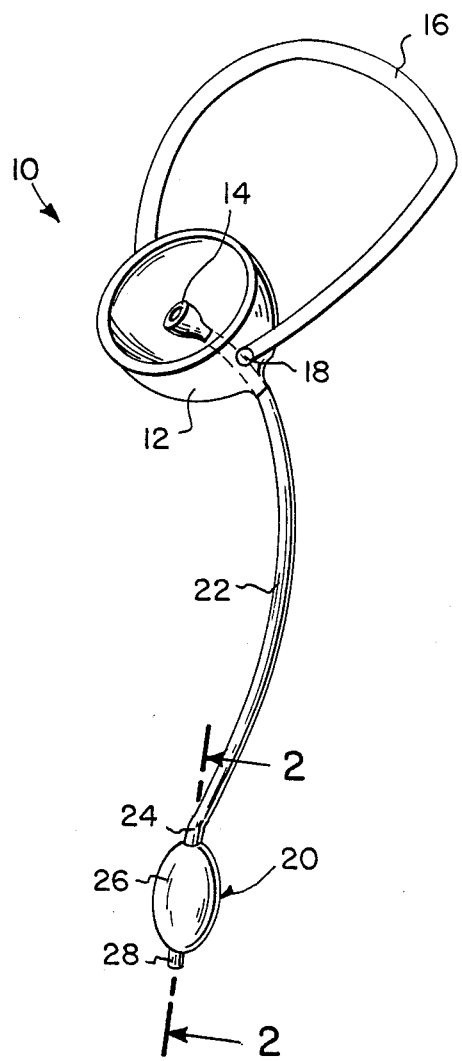
FIG. 1 is a perspective view of the invention.

Turning now descriptively to the drawings, in which similar reference characters denote similar elements throughout the several views, FIG. 1 illustrates an artificial respiration device 10 consisting of a mask 12 for covering a mouth of a person (not shown). A removable hollow nipple 14 is threaded within the mask 12. An elastic band 16 is affixed to the mask 12 by pivot snaps 18 so that the elastic band 16 can fit over the head of the person. The elastic band 16 secures the mask 12 over the mouth of the person with the nipple 14 extending into the mouth. A manually operated mechanism 20 is for supplying fresh air one-way through the nipple 14 and into lungs of the person so that the person can exit expired air back out through their nose into the ambient atmosphere.

Figure 2:
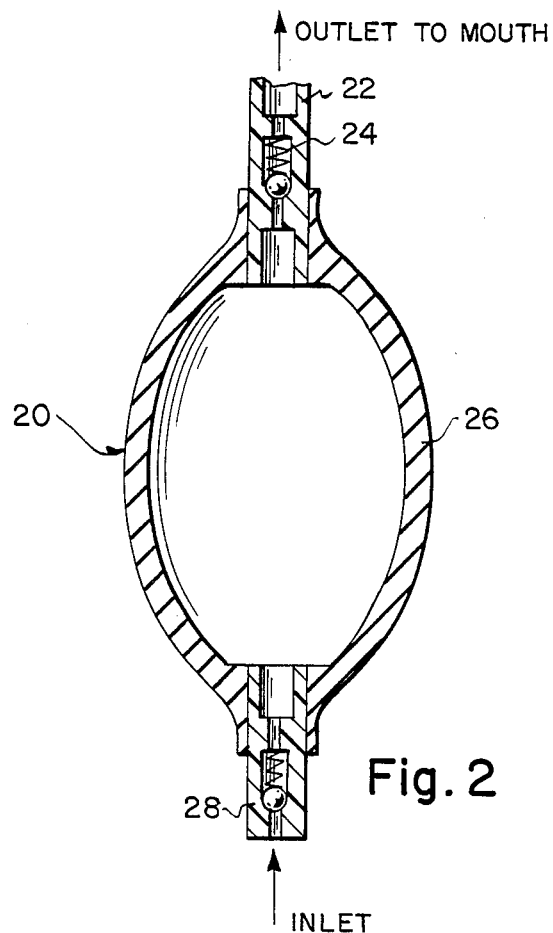
FIG. 2 is an enlarged cross sectional view taken along line 2—2 in FIG. 1 showing the bladder and air inlet and outlet valves in greater detail.

The mechanism 20, as best seen in FIG. 2, includes an elongated hollow tube 22 that has a first end fluidly connected to the nipple 14 and extends outwardly from the mask 12. A normally closed air outlet valve 24 is disposed within second end of the tube 22. A flexible compressible bladder 26 is connected to the second end of the tube 22. A normally closed air inlet valve 28 is connected to the bladder 26 opposite the air outlet valve 24 so that when the bladder 26 is manually compressed the air outlet valve 24 will open causing fresh air to move through the tube 22 and out of the nipple 14 into the lungs of the person. When the bladder 26 is released the air outlet valve 24 will close and the air inlet valve 28 will open allowing fresh air to re-enter the bladder 26 from the ambient atmosphere.

Figure 3:
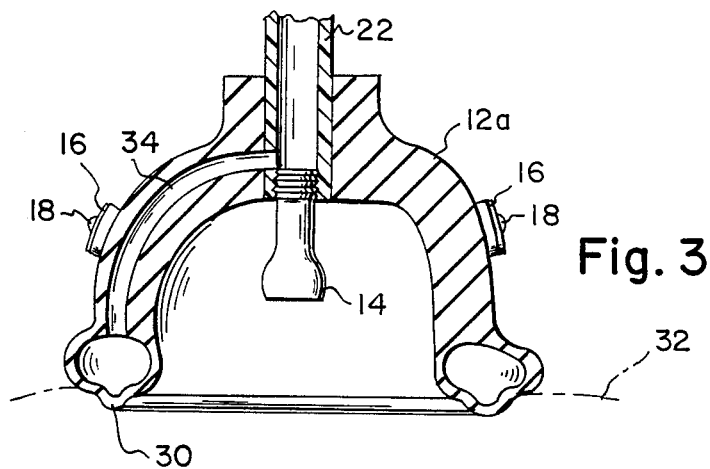
FIG. 3 is an enlarged cross sectional view of a modified mask in which a pipe runs between the elongated air tube and inflatable thin walled flange so that the flange will bear against face of a person during operation of the device.

FIG. 3 shows a modified mask 12a that includes an inflatable thin walled annular flange 30 adaptable to contact face 32 (shown in phantom) of the person about the mouth thereof. A flexible hollow pipe 34 is fluidly connected between side of the first end of the tube 22 within the mask 12a and the flange 30 whereby during operation of the device 10 a portion of the air from the tube 22 will cause the flange 30 to expand to bear against the face 32 of the person forming a tight seal therebetween.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An artificial respiration device which comprises:
  (a) a mask with an open peripheral end for covering a mouth of a person;
  (b) a removable hollow nipple threaded within said mask for insertion into a person's mouth;
  (c) means for securing said mask over the mouth of the person with said nipple extending into the mouth; and
  (d) means for manually supplying fresh air one way through said nipple and into lungs of the person so that the person can exit expired air back out through their nose into the ambient atmosphere; wherein said securing means is an elastic band affixed to said mask so that said elastic band can fit over head of the persons; wherein said fresh air supplying means includes:
  (e) an elongated hollow tube having a first end fluidly connected to said nipple within said mask and extending outwardly from said mask and a second end remote from said first end;
  (f) a normally closed air outlet valve disposed within said second end of said tube;
  (g) a flexible compressible bladder connected to said second end of said tube;
  (h) a normally closed air inlet valve connected to said bladder opposite said air outlet valve so that when said bladder is manually compressed said air outlet valve will open causing fresh air to move through said tube and out of said nipple into the lungs of the person and when said bladder is released said air outlet valve will close and said air inlet valve will open allowing fresh air to re-enter said bladder from the ambient atmosphere; wherein said mask includes:

(i) an inflatable thin walled annular flange adaptable to contact the face of the person about the mouth thereof; and (j) a conduit in said mask fluidly correcting the end of said tube within said mask and said inflatable flange whereby during operation of said device a portion of the air from the tube will cause said flange to expand to bear against the face of the person forming a tight seal therebetween.

* * * * *